United States Patent [19]
Kelly et al.

[11] Patent Number: 6,034,148
[45] Date of Patent: Mar. 7, 2000

[54] ENERGY ABSORBING FOAMS

[75] Inventors: David J. Kelly, Chadds Ford, Pa.; Beat Niederoest, Glassboro, N.J.

[73] Assignee: Foamex L.P., Linwood, Pa.

[21] Appl. No.: 09/001,388

[22] Filed: Dec. 31, 1997

Related U.S. Application Data

[63] Continuation-in-part of application No. 08/684,653, Jul. 19, 1996, Pat. No. 5,866,554.
[51] Int. Cl.[7] .............................. C08J 9/08; C08L 75/08; B29C 44/10; B29C 67/20
[52] U.S. Cl. .............................. 521/137; 264/51; 264/52; 521/174; 521/130; 523/347
[58] Field of Search ..................................... 521/137, 174, 521/130; 264/51, 52; 523/347

[56] References Cited

U.S. PATENT DOCUMENTS 4,777,186  10/1988  Stang et al. ................................. 521/50

FOREIGN PATENT DOCUMENTS 9309934  5/1993  WIPO .

*Primary Examiner*—Rabon Sergent
*Attorney, Agent, or Firm*—Connolly Bove Lodge & Hutz LLP

[57] ABSTRACT

Polyurethane foams formed at elevated pressure using a graft polyol, or mixture of polyols to form a polyol system, having a low functionality and a high solids content, exhibit superior dynamic shock cushioning characteristics (energy absorption) as illustrated by the drop curves of deceleration versus static load. The foam-forming ingredients are mixed together and foamed under controlled pressures in the range of 1.2 to 1.5 bar, preferably 1.3 to 1.4 bar. The polyol preferably has a functionality in the range of about 2.0 to 2.5, a hydroxyl number in the range of about 50 to 90, a solids content above about 35%, preferably about 50 to 55%.

12 Claims, 2 Drawing Sheets

ENERGY ABSORBING FOAMS

This application is a continuation-in-part of U.S. Ser. No. 08/684,653 filed Jul. 19, 1996, now U.S. Pat. No. 5,866,554.

This invention relates to flexible polyurethane foams used in shipping and packing cartons that isolate or reduce the effects from externally applied shocks or vibrations and thereby protect the contents of the carton.

BACKGROUND OF THE INVENTION

Cellular polyurethane structures typically are prepared by generating a gas during polymerization of a liquid reaction mixture comprised of a polyester or polyether polyol, a polyisocyanate, a surfactant, catalysts, and one or more blowing agents. The gas causes foaming of the reaction mixture to form the cellular structure.

Polyurethane foams with varying density and hardness may be formed. Hardness is typically measured as IFD ("indentation force deflection") or CFD ("compression force deflection"). Tensile strength, tear strength, compression set, air permeability, fatigue resistance, and energy absorbing characteristics may also be varied, as can many other properties. Specific foam characteristics depend upon the selection of the starting materials, the foaming process and conditions, and sometimes on the subsequent processing. Among other things, polyurethane foams are widely used as energy absorbing cushions and fillers in the packaging industry.

Once the foam-forming ingredients are mixed together, it is known that the foam may be formed under either elevated or reduced controlled pressure conditions. PCT Published Patent Application WO 93/09934 discloses methods for continuously producing slabs of urethane polymers under controlled pressure conditions. The foam-forming mixture of polyol, polyisocyanate, blowing agent and other additives is introduced continuously onto a moving conveyor in an enclosure with two sub-chambers. The foaming takes place at controlled pressure. Reaction gases are exhausted from the enclosure as necessary to maintain the desired operating pressure. The two sub-chambers, a saw, and airtight doors are operated in a manner that allows for continuous production of slabstock polyurethane foam.

U.S. Pat. No. 4,777,186 to Stang, et al., describes a method of foaming in a pressurized chamber held above atmospheric pressure (i.e., in the range of about 0.5 to 1000 psig). In addition to the gases emitted during foaming, additional gases may be introduced into the chamber to maintain the elevated pressure during foaming. The resulting foams have a higher ILD to density ratio than those previously known to the art.

Those of skill in the packaging industry characterize dynamic shock cushioning characteristics ("energy absorption") of materials by developing "drop curves" or plots of deceleration versus static load in accord with ASTM D 1056. A foam is cut to a predetermined size, typically 8"×8"×2" (thickness) and positioned on an impact surface. A dropping platen with an adjustable load is dropped onto the sample. Instrumentation measures both the peak impact deceleration ("G-level") and impact velocity as the platen deflects the cushion. The impact velocity is checked to be within tolerances, and the peak "G-level" is recorded. The impact velocity corresponds to a "free fall drop height," which is measured in order to compensate for the effect of friction in the dropping apparatus, but the corresponding free fall drop height is typically reported as if it were measured physically. The most commonly used free fall drop height is 24 inches. The platen, with the same static loading, is dropped on the same cushion five times. The static loading is calculated by dividing the mass of the platen by the surface area of the foam sample. Each drop is separated by about one minute. A new cushion sample is used, and a sequence of five drops is performed for another static loading, usually determined by the experience of the operator during the test. The process is repeated until enough data points have been gathered to draw a representative curve. The average of the second through fifth drops is commonly reported as the average "G-level" for each static loading. Lower "G-levels" indicate greater energy absorption by the foam, or less shock felt by the platen or what would be the packaged object in packaging applications. Prior art packaging materials using a two-inch sample thickness and a 24-inch "free fall drop height" generally yield G-levels above 60 G at a 1 psi static loading.

An object of the present invention is to produce energy absorbing foams with "drop curves" substantially improved over those previously obtained in the prior art. Where foams with improved "drop curves" are used in packaging applications, either less foam is required for the same energy absorbing protection, or the foam may be used to package heavier objects than previously possible.

SUMMARY OF THE INVENTION

According to the invention, foams with improved energy absorption are obtained by a method in which a foam-forming composition of:

(a) a graft polyol, or a polyol system formed as a mixture of graft polyols or graft polyols and polyether polyols, where the polyol or polyol system has an average functionality in the range of about 2.0 to 2.5, an average hydroxyl number in the range of about 50 to 90, and an average solids content above about 35%;

(b) from about 20 to 90 parts by weight, based upon 100 parts by weight polyol, of a polyisocyanate;

(c) water as a blowing agent;

(d) one or more surfactants; and (e) one or more catalysts;

is mixed together and foamed under controlled pressure conditions from about 1.2 to about 1.5 bar, preferably 1.3 to 1.4 bar. Preferably, the polyol is a low functionality, low molecular weight graft polyol, with a high solids content in the range of about 35% to 55%, such as BASF TF21710. Preferably, the polyisocyanate is toluene diisocyanate (TDI) at an index from 110 to 130.

Surprisingly, foams prepared according to this invention exhibit excellent energy absorbing characteristics over those of prior art foams. The resulting foams have a density in the range of about 1.0 to 4.0 pounds per cubic foot, most preferably 2.2 to 2.8 pounds per cubic foot, a permeability in the range of between about 20 to 140 $ft^3/ft^2/min$, most preferably between about 50 to 110 $ft^3/ft^2/min$, and 25% no pre-flex CFD of about 7 to 13 psi, most preferably 9 to 11 psi.

DESCRIPTION OF THE PREFERRED EMBODIMENT

Figure 1:
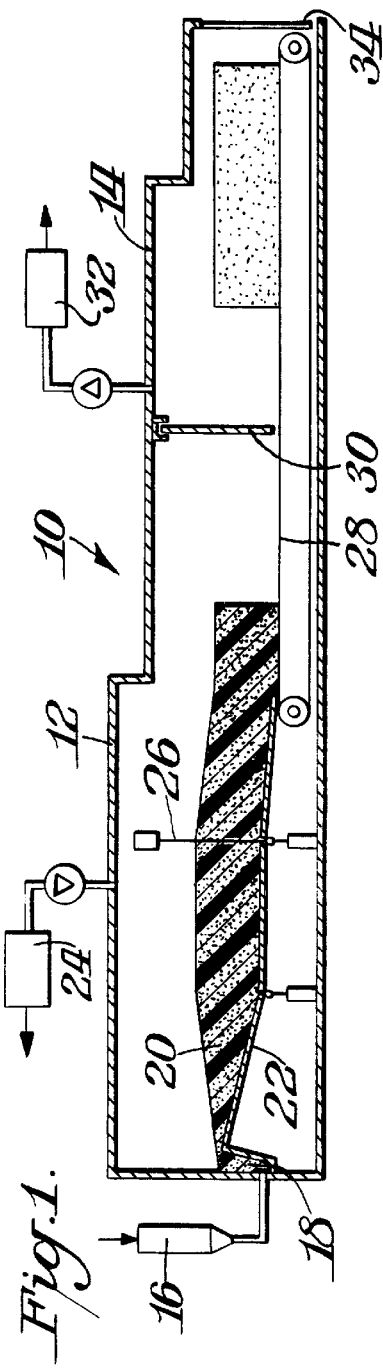
FIG. 1 is a schematic drawing of an apparatus that may be used to foam under controlled pressure.

Polyether polyols having a functionality of at least 2.0 are known to be suitable for producing flexible polyurethane foams. Polyether polyols used to prepare flexible polyurethane foams typically have molecular weights between 500 and 7000. Examples of these polyols are VORANOL 3010 from Dow Chemical and PLURACOL 1103 from BASF. Graft or modified polyether polyols contain dispersed polymeric solids. The solids increase hardness and mechanical strength of the resultant foam. An especially preferred polyol in this invention is a low functionality graft polyol supplied by BASF as BASF TF21710.

The term "polyether polyol" includes linear and branched polyethers (having ether linkages) and containing at least two hydroxyl groups, and includes polyoxypropylene polyether polyol or mixed poly(oxyethylene/oxypropylene) polyether polyol. Preferred polyethers are the polyoxyalkylene polyols, particularly the linear and branched poly (oxyethylene)glycols, poly(oxypropylene)glycols and their copolymers. Graft or modified polyether polyols are those polyether polyols having a polymer of ethylenically unsaturated monomers dispersed therein. Representative modified polyether polyols include polyoxypropylene polyether polyol into which is dispersed poly(styrene acrylonitrile) or polyurea, and poly(oxyethylene/oxypropylene)polyether polyols into which is dispersed poly(styrene acrylonitrile) or polyurea. Graft or modified polyether polyols are commercially available from several companies. Those from BASF include TF21710 and 1103.

The "hydroxyl number" for a polyol is a measure of the amount of reactive hydroxyl groups available for reaction. The value is reported as the number of milligrams of potassium hydroxide equivalent to the hydroxyl groups found in one gram of the sample. "Functionality" of a polyol is defined as the average number of isocyanate reactive sites per molecule.

The term "polyisocyanate" refers particularly to isocyanates that have previously been suggested for use in preparing polyurethane foams. "Polyisocyanates" include di- and polyisocyanates and prepolymers of polyols and polyisocyanates having excess isocyanate groups available to react with additional polyol. The amount of polyisocyanate employed is frequently expressed by the term "index" which refers to the actual amount of isocyanate required for reaction with all of the active hydrogen-containing compounds present in the reaction mixture multiplied by 100. For most applications, the index is in the range of about 75 to 140.

Conventional polyisocyanates may be used in this invention. The preferred isocyanate is toluene diisocyanate (TDI), particularly including TD80, a commercially available blend of 80% of 2,4 toluene diisocyanate and 20% of 2,6 toluene diisocyanate. Polyisocyanates are typically used at a level of between about 20 and 90 parts by weight per 100 parts of polyol, preferably between 35 and 45 parts in this invention.

Catalysts are used to control the relative rates of water-polyisocyanate (gas forming) and the polyol-polyisocyanate (gelling) reactions. The catalyst may be a single component, or in most cases, a mixture of two or more compounds. Preferred catalysts for polyurethane foam production are organotin salts and tertiary amines. The amine catalysts are known to have a greater effect on the water-polyisocyanate reaction, whereas the organotin catalysts are known to have a greater effect on the polyol-polyisocyanate reaction. Total catalyst levels vary from about 0.01 to 5.0 parts by weight per 100 parts of polyol. The amount of catalyst used depends upon the formulation employed and the type of catalyst, as known to those skilled in the art. Although various forms of catalysts may be used in the present invention, control of the gelling catalyst level is critical to the air permeability of the final foam. Air permeability is known to significantly affect the energy absorbing characteristics.

One or more surfactants are also employed in the foam-forming composition. The surfactants lower the bulk surface tension, promote nucleation of bubbles, stabilize the rising cellular structure and emulsify incompatible ingredients. The surfactants typically used in polyurethane foam applications are polysiloxane-polyoxyalkylene copolymers, which are typically used at levels of between about 0.5 and 3 parts by weight per 100 parts of polyol.

Optionally, other additives may be incorporated into the foam-forming composition. The optional additives include, but are not limited to, fire retardants, stabilizers, antimicrobial compounds, dyes, pigments, and antistatic agents. Such additives should not have any detrimental effect on the properties of the final polyurethane foam.

The foam-forming process may be carried out batch-wise, semi-continuously or continuously, as long as the pressure may be controlled and maintained above atmospheric pressure, preferably in the range of 1.3 to 1.4 Bar.

FIG. 1 shows an apparatus that might be used to practice the invention in a continuous process, which is taken from the disclosure in WO 93/09934. In such an apparatus 10, there is a process subchamber 12 and an adjacent airlock subchamber 14. The subchambers 12, 14 are separated from one another by door 30. Foam-forming ingredients are introduced to mix head 16 and mixed for a suitable time. Once mixed together, the foam-forming ingredients form a frothing liquid that is introduced to the bottom of trough 18 flow onto the fall plates 22. The foam rises as it is conveyed away from the trough. After the foam is completely risen, a slab 25 is then cut from the foamed material using cut off blade 26. The slab 25 is conveyed by the moving conveyor 28. Fan 24 exhausts process gases to maintain the pressure within the process enclosure 12. The first door 30 opens to allow the slab 25 into the airlock enclosure 14. The door 30 closes and the pressure inside the airlocked chamber is returned to atmospheric conditions. A second exhaust fan 32 removes additional process gases. The foam slab 25 exits the airlock enclosure 14 through door 24. The airlock chamber 14 is returned to the operating pressure and the process continues.

The invention is further illustrated, but not limited by, the following examples.

EXAMPLES

Foams were prepared batchwise on a laboratory scale in a fixed head foam machine with the formulations listed in Table I. The water, isocyanate, polyol, and additives were poured from the fixed mixing head into a box positioned inside a pressurized chamber. The pressure was elevated above atmospheric pressure by pumping air into the chamber. Using a pressure regulator, the pressure was maintained at the operating pressure while the foam was allowed to rise. Air was released from the chamber to compensate for the additional gas generated by the foaming mixture. In the case of foams made at 1 Bar pressure, the boxes were located outside the chamber as pressure control was not necessary.

Drop curves were developed for each material using the test method of ASTM D 1056. Air permeability was determined in cubic feet per square foot per minute of a sample using a Frazier Differential Pressure Air Permeability Pressure Machine in accord with ASTM D 737. CFD or "Compressive Force Deflection" was determined in accord with a procedure similar to ASTM D 3574. CFD is a measure of the force a 2"×2"×1" sample exerts against a circular compression plate having a 3.5" diameter. In this case, the foam was compressed by 25% of its original height and the force was reported after 1 minute. The only difference between the ASTM D 3574 test and the test performed on these samples is that the ASTM standard specifies that two 80% "preflexes" or precrushes of the foam should be performed before the testing is carried out. These preflexes are normally omitted from the procedure when CFD is determined for foams with high hardness, as these foams tend to require more time to recover their full height after compression.

Figure 2:
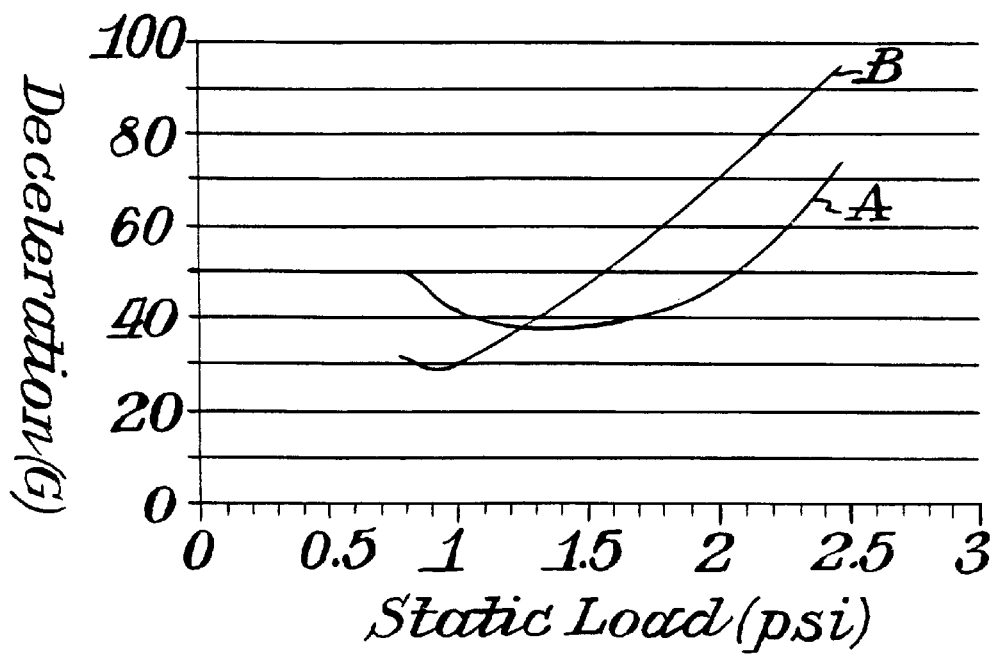
FIG. 2 is a graph of deceleration versus static loading comparing the dynamic cushioning curve for foam prepared according to the invention with the curve for foam of substantially equivalent chemical composition prepared at atmospheric conditions.

FIG. 2 displays the unexpected improvement in dynamic cushioning when pressurized chamber conditions are used. Formulation A was produced with an operating pressure of 1.3 Bar, and Formulation B with an operating pressure of 1 Bar. The polyol, polyisocyanate index, amine catalyst, and surfactant were held constant in both formulations. The water level was adjusted such that the resulting densities of the two foams would be approximately the same. By adjusting the density, the results demonstrate that density alone does not control the energy absorbing performance. Formulation B actually has a slightly higher density. The organotin catalyst was adjusted such that the resulting air permeabilities of the two foams would also be approximately the same.

As can be seen from FIG. 2, the foam produced at 1.3 Bar yields substantially lower G-levels at high static loadings. This greater energy absorbing effectiveness translates into a performance advantage for packaging. If a package were designed such that the enclosed object would be subjected to no more than 60 G, then a static loading of no more than about 1.8 psi could be used if the foam from Formulation B were selected (at a two-inch thickness for a 24-inch drop height). By contrast, a higher static loading of about 2.3 psi loading could be used if the foam from Formulation A were selected (at a two-inch thickness for a 24-inch drop height). This is more than a 20% reduction in the foam surface area required, and therefore translates to more than a 20% foam material savings. Both Formulations A and B were prepared with the preferred polyol, BASF TF21710.

Figure 3:
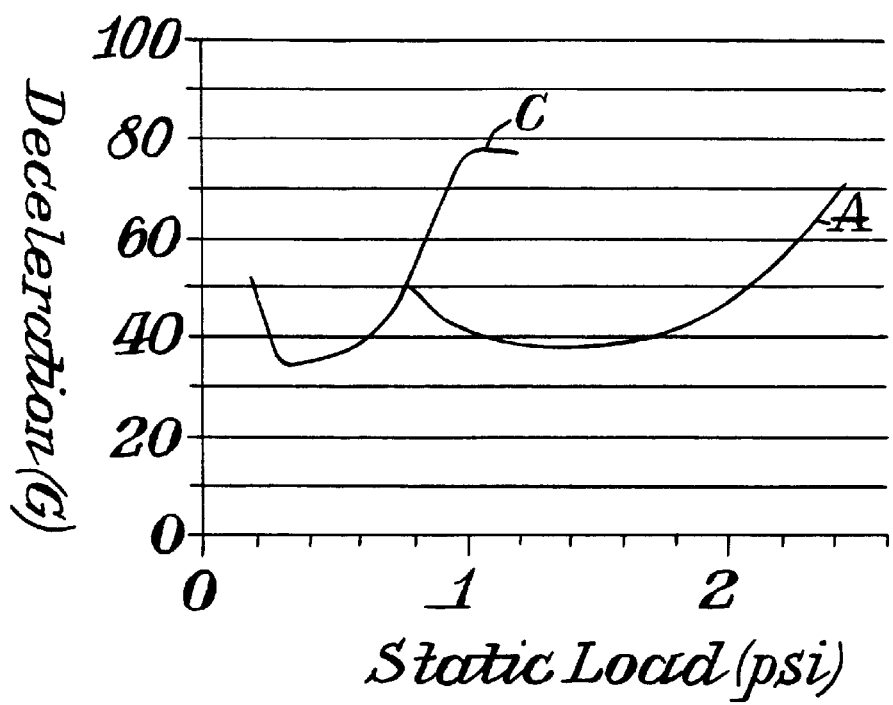
FIG. 3 is a graph of deceleration versus static loading comparing the dynamic cushioning curves for foam prepared according to the invention with curves for foam prepared by the method described in Example 12 of U.S. Pat. No. 4,777,186.

FIG. 3 compares Formulation A to a foam produced by the method disclosed in Example 12 of U.S. Pat. No. 4,777,186 (Formulation C in Table I below). As shown in FIG. 3, the use of pressurized operating conditions alone does not yield foams with the same energy absorbing or drop curve performance advantage. It is the elevated pressure conditions combined with the specific low functionality, high solids content graft polyols that produces the foams with the superior energy absorbing and drop curve performance. Referring to FIG. 3, if one were to design a package with a target 60 G level, a 2.2 psi static loading is possible with Formulation A, whereas only a much lower 0.8 psi static loading is possible with Formulation C. The foam produced using Formulation A thus offers 175% material reduction over the foam produced using Formulation C.

Hardness (CFD) of the foam produced using Formulation A is substantially higher than that produced using Formulation C. U.S. Pat. No. 4,777,186 speaks of the ability to produce foams with a higher hardness/density ratio using pressurized foaming conditions. While energy absorbing characteristics may in part result from higher hardness, the inventive foams according to the invention (using the combination of specific graft polyols and pressurized foaming conditions) unexpectedly achieve much greater energy absorbing (drop curve) performance.

Figure 4:
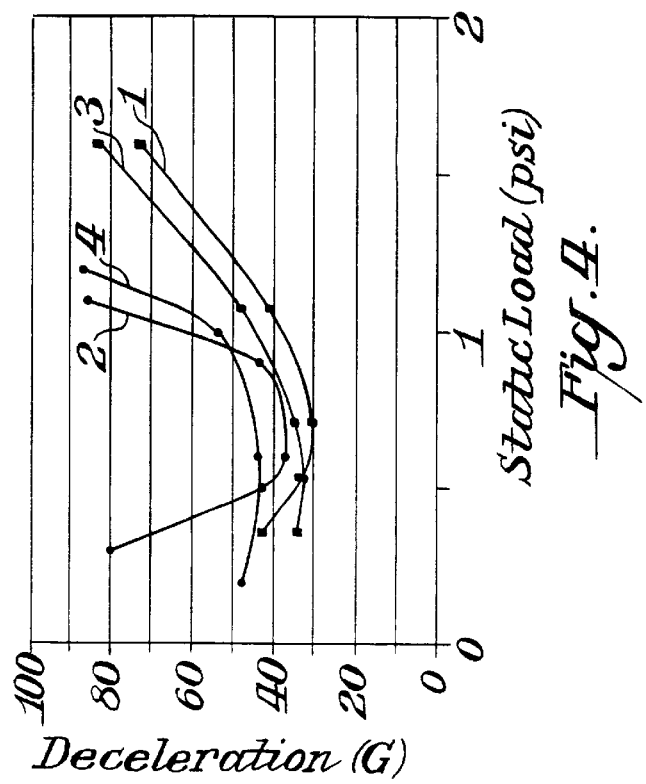
FIG. 4 is a graph of deceleration versus static loading comparing the dynamic cushioning curves for foams prepared with a low functionality graft polyol to those prepared with a higher functionality graft polyol, and under atmospheric and pressurized conditions.

Formulations D and E were produced using a preferred graft polyol (BASF TF21710), and Formulations F and G were produced using a conventional graft polyol (BASF 1103). The formulations were adjusted such that in addition to the density and air permeability being about the same at each pressure, also the hardness (CFD) was held nearly constant at each pressure. As shown in FIG. 4, Formulation D (1.3 Bar and BASF TF21710) is compared to Formulation F (1.3 Bar and BASF 1103), there is an unexpected significant improvement with Formulation D. Formulation D yields lower G-levels at higher static loadings, despite the nearly equivalent physical properties of the foams.

Moreover, again referring to FIG. 4, the foam from Formulation D shows a much greater improvement in dynamic cushioning as compared to the foam made from a substantially equivalent composition but foamed at atmospheric pressure (Formulation E), than does the conventional graft polyol foam made at higher pressure (Formulation F) as compared to the comparable foam made at atmospheric pressure (Formulation G). These examples demonstrate that the combination of special polyols and foaming under pressure achieves unexpectedly superior results.

TABLE I

| Formulation | A | B Comparison | C Comparison | D | E Comparison | F Comparison | G Comparison |
|---|---|---|---|---|---|---|---|
| Polyol: BASF TF21710 | 100 | 100 | 0 | 100 | 100 | 0 | 0 |
| Polyol: BASF 1103 | 0 | 0 | 80 | 0 | 0 | 100 | 100 |
| Polyol: BASF 3010 | 0 | 0 | 20 | 0 | 0 | 0 | 0 |
| Water | 2.7 | 1.7 | 2.3 | 2.77 | 2.77 | 2.6 | 2.6 |
| Amine catalyst: ZF-53 | 0.1 | 0.1 | 0.11 | 0.1 | 0.2 | 0.11 | 0.12 |
| Organotin catalyst: C9N | 0.4 | 0 | 1.0 | 0.95 | 0 | 1.38 | 1.08 |
| Organotin | 0 | 0.26 | 0 | 0 | 0.06 | 0 | 0 |

TABLE I-continued

| Formulation | A | B Comparison | C Comparison | D | E Comparison | F Comparison | G Comparison |
|---|---|---|---|---|---|---|---|
| catalyst: C2 | | | | | | | |
| Silicone surfactant: L618 | 1.0 | 1.0 | 1.0 | 1.0 | 1.0 | 1.0 | 1.0 |
| Polyisocyanate: TD80 | 44.5 | 33.2 | 33.1 | 40.6 | 40.4 | 35.6 | 35.6 |
| Index | 120 | 120 | 120 | 106 | 106 | 120 | 120 |
| Pressure (Bar) | 1.3 | 1.0 | 1.43 | 1.3 | 1.0 | 1.3 | 1.0 |
| Density (lb/ft$^3$) | 2.76 | 2.88 | 3.26 | 2.52 | 1.83 | 2.61 | 2.08 |
| ½" Permeability | 77.6 | 79.6 | 82.8 | 43.2 | 42.5 | 28.8 | 50 |
| CFD (25%) (no preflex) | 9.85 | 3.8 | 3.18 | 3.92 | 2.58 | 4.03 | 2.77 |

The invention has been illustrated by detailed description and examples of the preferred embodiment. Various changes in form and detail will be within the skill of persons skilled in the art. Therefore, the invention must be measured by the claims and not by the description of the examples or the preferred embodiments.

We claim:

1. A method for producing an energy-absorbing polyurethane foam, comprising the steps of:

(1) preparing a foam-forming composition from (a) a graft polyol having a functionality of between about 2.0 and 2.5, a hydroxyl number in the range of about 50 to 90, and a solids content at least 35% by weight, and (b) from about 20 to 90 parts by weight, based upon 100 parts by weight polyol, of a polyisocyanate, (c) water as a blowing agent, (d) a surfactant; and (e) a catalyst; and (2) forming the polyurethane foam from the foam-forming composition under controlled pressure conditions from about 1.2 to about 1.5 bar (absolute).

2. The method for producing a polyurethane foam of claim 1, wherein the polyurethane foam is formed under a controlled pressure of about 1.3 to 1.4 bar (absolute).

3. The method for producing a polyurethane foam of claim 1, wherein the isocyanate index is from about 110 to 130.

4. The method for producing a polyurethane foam of claim 1, wherein the polyol is a polyol system formed as a mixture of graft polyols or graft polyols with polyether polyols such that the polyol system has an average functionality of between about 2.0 and 2.5, an average hydroxyl number in the range of about 50 to 90, and an average solids content of at least 35% by weight.

5. The method for producing a polyurethane foam of claim 1, wherein the resulting foam has a density in the range of between about 1.0 to 4.0 pounds per cubic foot.

6. The method for producing a polyurethane foam of claim 5, wherein the resulting foam has a density in the range of between about 2.2 to 2.8 pounds per cubic foot.

7. The method for producing a polyurethane foam of claim 1, wherein the resulting foam has an air permeability in the range of between about 20 to 140 ft$^3$./ft$^2$/min.

8. The method for producing a polyurethane foam of claim 7, wherein the resulting foam has an air permeability in the range of between about 50 to 110 ft$^3$./ft$^2$/min.

9. The method of producing a polyurethane foam of claim 1, wherein the polyol has a solids content of about 35% to 55% by weight.

10. The method of producing a polyurethane foam of claim 9, wherein the polyol has a solids content of about 50% to 55% by weight.

11. A polyurethane foam produced according to the method of claim 1.

12. A polyurethane foam produced according to the method of claim 4.

* * * * *

UNITED STATES PATENT AND TRADEMARK OFFICE
CERTIFICATE OF CORRECTION

PATENT NO. : 6,034,148
DATED : Mar. 7, 2000
INVENTOR(S) : David J. Kelly and Beat Niederoest It is certified that error appears in the above-identified patent and that said Letters Patent is hereby corrected as shown below:

On the cover page, the FUTURE FOAM Product Brochure "Future Pack™" should be listed among the References Cited.

On the cover page, the "Continuation-in-part of application 08/684,653, Jul.19,1996, Pat. No. 5,866,554." reference should be removed from the list of Related U.S. Application Data.

Column 1, Line 3-4 please delete "This application is a continuation-in-part of U.S. Ser. No. 08/684,653 filed Jul.19,1996, now U.S. Pat. No. 5,866,554."

Signed and Sealed this

Twenty-fourth Day of April, 2001

Attest:

NICHOLAS P. GODICI

Attesting Officer

Acting Director of the United States Patent and Trademark Office